United States Patent [19]
Ablaza

[11] 4,190,909
[45] Mar. 4, 1980

[54] APPARATUS AND METHOD FOR SURGICAL REPAIR OF DISSECTING THORACIC ANEURYSMS AND THE LIKE

[76] Inventor: Sariel G. G. Ablaza, 1335 W. Tabor Rd., Philadelphia, Pa. 19141

[21] Appl. No.: 892,191

[22] Filed: Mar. 31, 1978

[51] Int. Cl.² ............................ A61F 1/24; A61F 1/00
[52] U.S. Cl. ...................................... 3/1.4; 128/334 R
[58] Field of Search ...................... 3/1.4, 1; 128/334 R, 128/334 C

[56] References Cited

U.S. PATENT DOCUMENTS

| | | | |
|---|---|---|---|
| 3,254,651 | 6/1966 | Collito | 128/334 C |
| 3,818,515 | 6/1974 | Neville | 3/1 |
| 3,889,685 | 6/1975 | Miller, Jr. et al. | 128/334 R X |
| 4,047,252 | 9/1977 | Liebig et al. | 3/1.4 |

OTHER PUBLICATIONS

"New Surgical Technique for the Operative Management of Acute Dissections of the Ascending Aorta," by G. Dureau et al., The Journal of Thoracic & Cardiovascular Surgery, vol. 76, No. 3, Nov. 1978, pp. 385-389. Blood Vessel Tubes–Blakemore–Lord Type, Arterial Anastomosis Tubes, Catalog No. 6491, Vitallium Surgical Appliances (catalog), Austenal Laboratories, Inc., Mar. 1948, p. 22.

*Primary Examiner*—Ronald L. Frinks
*Attorney, Agent, or Firm*—Arthur A. Jacobs

[57] ABSTRACT

A prosthetic graft in the form of a flexible tube with rigid end portions, wherein the rigid end portions each have an annular groove. The graft is used by slitting the portion of an artery containing an aneurysm or other damage to form an opening, inserting the graft through the opening into the artery, positioning the graft longitudinally within the artery, and circumferentially ligating the artery against the grooves in the rigid end portions of the graft.

6 Claims, 11 Drawing Figures

APPARATUS AND METHOD FOR SURGICAL REPAIR OF DISSECTING THORACIC ANEURYSMS AND THE LIKE

This invention relates to a surgical device and a process for utilization of such device, and it particularly relates to a prosthetic graft for the repair of ducts in a living body, such as the arterial system.

A significant cause of disability and death throughout the history of mankind has been damage to a portion of the arterial system which carries blood from the heart to the various parts of the body. This has been a particular problem with regard to aneurysms in the aorta which is the main trunk of the arterial system and which conveys blood from the left ventricle of the heart to all of the body except the lungs.

In recent years, a great advance has been made in the medical, and, particularly, in the surgical arts, whereby the portion of the artery or aorta in which the aneurysm occurs is cut away or "resected" and a tubular "graft" is substituted for the resected segment. This graft is generally a fabric tube, corresponding in diameter to the resected artery segment. The tubular graft, after it is set in place, is then sutured at it's opposite ends to the adjacent edges of the artery defining the space resulting from the resected segment.

Although, as stated above, this procedure has constituted a major development in the field of medicine, there have been various problems connected therewith. In this respect, a primary problem has been that the sutures connecting the graft to the artery have sometimes torn away or disintegrated. Even worse, the sutures have, at times, ripped away the tissue at the sutured edges of the artery. This has resulted in blood seepage or even total rupture of the arterial walls at the areas of suture, with obviously dire results.

Among various attempts to solve the above problem, it has been proposed to avoid resection of the segment containing the aneurysm, whereby the segment is left in place but is cut open and the graft is inserted through the opening, where it is aligned coaxially within the artery. The graft is then sutured at its ends to the arterial areas adjacent thereto. This constituted a significant improvement over the resected technique, but there was still a tendency of the sutures to tear or disintegrate, so that the danger of seepage or even greater loss of blood remained a problem, because if the connection of the graft to the arterial walls was disrupted, not only did the aneurysm become exposed, but a loose graft within the artery could form an extremely dangerous blockage to the vital blood flow.

It is one object of the present invention to overcome the above problems by providing a graft and a method of using it which obviates the necessity of resection and which utilizes the arterial walls of the segment containing the aneurysm or other defects to reinforce and strengthen the graft.

Another object of the present invention is to provide a graft and method of using it which obviates the use of sutures and wherein fixation of the graft is achieved by ligating the graft to the arterial tissue and causing ingrowth of the tissue into the graft to create a permanent bond.

Other objects and many of the attendant advantages of this invention will be readily appreciated as the same becomes better understood by reference to the following description when read in conjunction with the accompanying drawings wherein.

Figure 1:
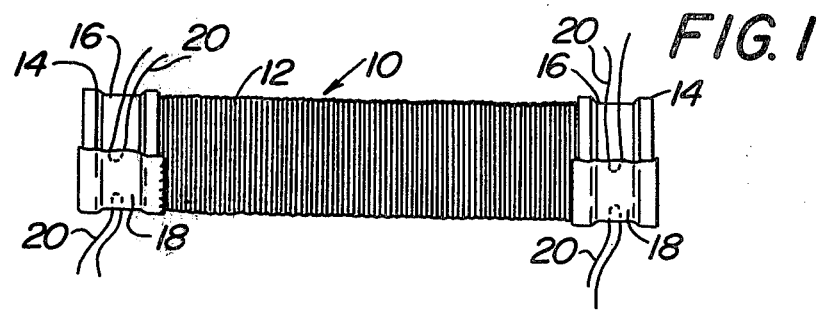
FIG. 1 is a side elevational view of a graft embodying the present invention.
Figure 2:
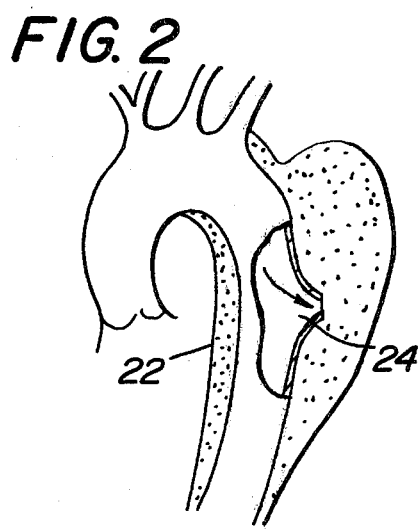
FIG. 2 is a side view, partly in elevation and partly in section, of the descending aorta containing an aneurysm.
Figure 3:
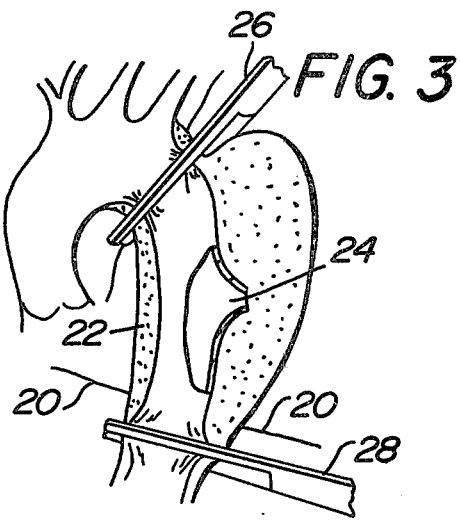
FIG. 3 is a view similar to FIG. 2 but showing the first step of the surgical procedure wherein the aorta is cross-clamped proximal and distal to the aneurysm.

Referring in greater detail to the figures of the drawings wherein similar reference characters refer to similar parts, there is shown in FIG. 1 a graft, generally designated 10, which comprises a woven tube 12 constructed of a synthetic polyester, such as "Dacron", and having a stainless steel ring 14 at each end of the tube. The rings 14 are each provided with a central groove 16 and are covered by a knitted velour covering 18, also made of "Dacron" or the like. The covering 18 encapsulates the ring by means of overlapping lip portions which are enfolded around the edges of the ring. The encapsulated rings are attached to the tube by sewing or suturing the overlapped lip portions of the covering 18 to the body of the tube. In this manner, the metal of the rings is completly out of contact with the tissue of the artery. A nylon ligature 20 is passed through the covering 18 at each end of the graft by a needle (not shown) so that the two lengths of the ligature dangle free.

The above-described construction of the graft not only prevents contact of the metal with the tissue but also has the characteristics whereby the woven tubular body has very low pososity and obviates any necessity for pre-clotting to avoid blood seepage, while the knitted velour portion permits the tissue to ingrow into it and provides a permanent bond after the graft is in place.

Figure 4:
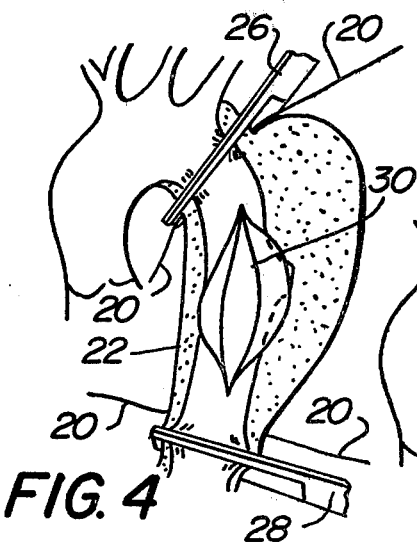
FIG. 4 is a view similar to FIG. 2 but showing the opening which is slit longitudinally of the aorta segment for insertion of the graft.
Figure 5:
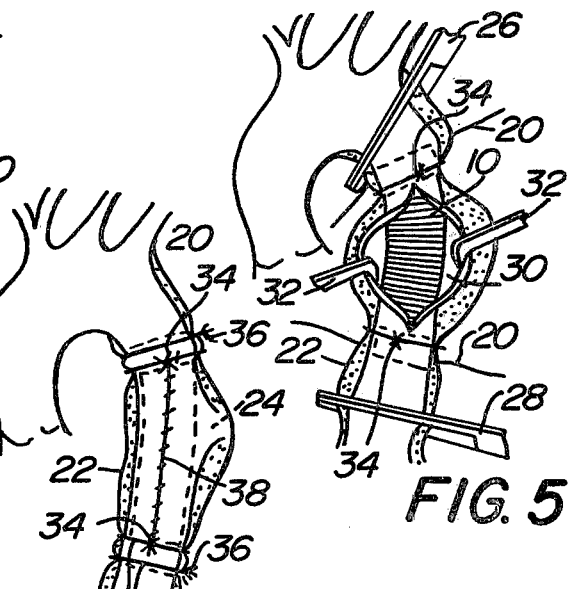
FIG. 5 is a view similar to FIG. 4 but showing the graft positioned in the aorta segment after it has been inserted through the opening.
Figure 6:
FIG. 6 is a view similar to FIG. 5 but showing the completed repair with the opening closed.
Figure 7:
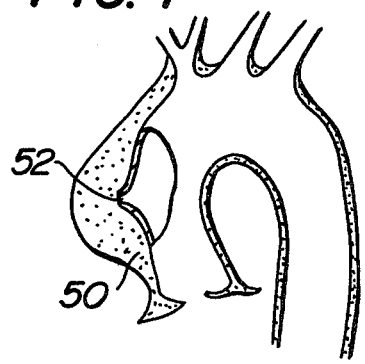
FIG. 7 is a side view, partly in elevation and partly in section, of an ascending aorta containing an aneurysm.
Figure 8:
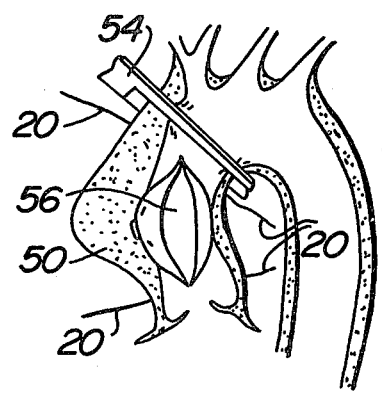
FIG. 8 is a view similar to FIG. 7 but showing the first and second steps of the surgical procedure wherein the opening is slit into the aorta segment.

The procedure used in repairing an aneurysm in the descending aorta is shown in FIGS. 2 to 6. The descending aorta is indicated at 22 and the aneurysm is indicated at 24. In the first step of the procedure, shown in FIG. 3, clamps 26 and 28 are applied proximal and distal to the aneurysm 24. Then, as shown in FIG. 4, a longitudinal opening 30 is slit in the segment of the aorta 22 between the clamps and adjacent the aneurysm. Then, as shown in FIG. 5, forceps 32 are applied to stretch the opening 30 wide and the graft 10 is inserted through the opening 30 and manipulated into the longitudinal position internally of the aorta and coaxial therewith. With the graft in position, the ligatures 20 are passed through the aorta tissue by the needles (not shown), after which one length of each ligature is wound around the outside of the aorta within the area defined by the corresponding grooves 16, then tied in place, as indicated at 34. Then the second length of each ligature is wound around the outside of the aorta and tied in place, as indicated at 36 in FIG. 6. The grooves 16 cause the ligatures 20, when tightly engaged, to be positioned within the channels in the aorta that are defined by the underlying grooves 16 so that the ribs on the rings 14, that define the grooves 16, form ridges in the aorta which prevent lateral slippage of the ligatures. Thereafter, the forceps are removed, the opening 30 is sutured together, with the native aorta fitting snugly around the graft, as shown at 38 in FIG. 6, and the clamps 26 and 28 are removed.

In the above manner, a secure repair is made of the damaged aorta in such a way that not only is it not necessary to resect any portion of the aorta but the native aorta segment, containing the aneurysm itself, acts as a reinforcement for the graft. Furthermore, since there are no sutures connecting the ends of the graft to any edges of the aorta, such as would define a gap caused of a resected segment, there is no danger of such edges becoming torn away from the sutures or of the sutures tearing or disintegrating. The only sutures are those used to close the opening, as at 38, but these sutures even if accidentally damaged, would have no real effect on the repair since the blood flow would still pass through the graft and the graft would still be secured by the threads 20. In addition, in time, the surrounding tissue would grow into the velour coverings 18 of the graft, thereby making the threads generally superfluous.

FIGS. 7 to 11 show the same general procedure as above, but are used in the repair of the ascending aorta. In this respect, the ascending aorta is shown at 50 and contains an aneurysm 52. In the first steps, shown in FIG. 8, a clamp 54 is cross-clamped distal to the aneurysm. It is not necessary in this instance to cross-clamp proximal because of the direction of blood flow. An opening 56 is then slit into the ascending aorta adjacent the aneurysm.

Figure 9:
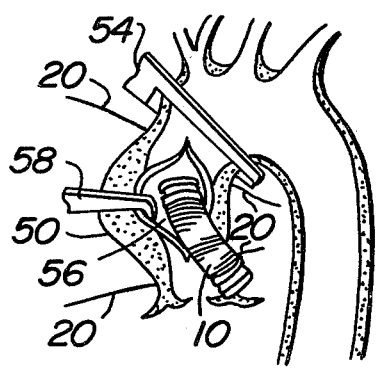
FIG. 9 is a view similar to FIG. 8 but showing the graft being inserted through the opening.
Figure 10:
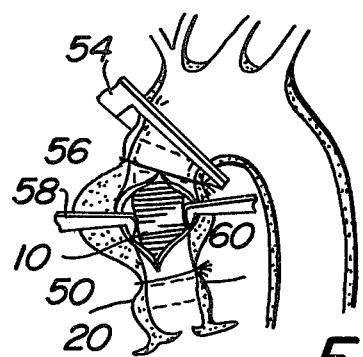
FIG. 10 is a view similar to FIG. 9 but showing the graft in place and the aorta ligated around the rings of the graft.
Figure 11:
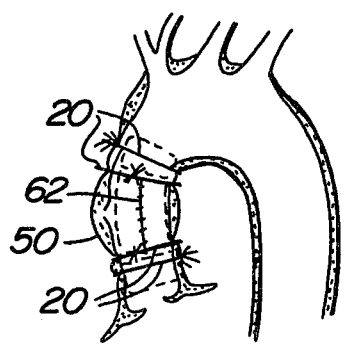
FIG. 11 is a view similar to FIG. 10 but showing the opening closed and the repair completed.

As shown in FIGS. 9 and 10, forceps 58 and 60 are used to stretch the opening 56 to permit easy entrance of the graft 10. The graft is then positioned longitudinally within the aorta and the ligatures, which have been passed through the aorta tissue, are wrapped around the exterior of the aorta within the channels defined by the grooves 16 of the graft, and are then tied in place, in the same manner as described above. The opening 56 is then sutured together, as shown at 62 in FIG. 11.

Although the rings 16 are constructed of stainless steel and although this is the preferred material because of the inherent characteristics of strength, non-corrosiveness, and the like, it is possible to use other materials such as plastics or other metals, when such other materials are found feasible. The same is generally true of the materials used for the construction of the tubular body 12 and the coverings 18. It is furthermore, to be understood that although this invention has been described with reference to the repair of arterial ducts having an aneurysm, it may also be utilized for the repair of such ducts which may be otherwise damaged, or for ducts other than arterial ducts within the body. In addition, the invention is applicable to both human and other living bodies. It is also possible to use separate ligatures rather than ligatures connected to the graft, although the connected ligatures are preferable because, after they are passed through the duct tissue, they can be used to align and retain the graft in position within the duct.

The invention claimed is:

1. A prosthetic graft comprising a flexible tubular body having a rigid, non-flexible ring at each of its two opposed ends, each ring defining an opening into the tubular body, each of said rings having an annular groove on its outer periphery which is defined by an annular rib at each side thereof, a flexible cover encapsulating each of said rings, said tubular body being constructed of a woven fabric and said cover being constructed of a knitted velour fabric.

2. A method of repairing damaged ducts within a living body which comprises forming an opening in the duct adjacent the damage, inserting a tubular prosthetic graft through the opening into the duct and positioning the graft coaxially of and within the duct, the graft comprising a flexible tubular body having a rigid non-flexible ring at each end, each ring defining an opening into the tubular body, each ring having an annular groove on its outer periphery which is defined by an annular rib at each side thereof, and a flexible cover encapsulating each ring, then wrapping around and tying ligatures around the exterior of the duct within channels formed in the duct corresponding to the grooves in the rings of the graft, and, finally, suturing the opening in the duct closed.

3. The method of claim 2 wherein the duct is an artery.

4. The method of claim 2 wherein the duct is an ascending aorta.

5. The method of claim 2 wherein the duct is a descending aorta.

6. The method of claims 2 wherein the damage in the duct is an aneurysm.

* * * * *